(12) United States Patent
Stefanon

(10) Patent No.: US 10,641,755 B2
(45) Date of Patent: May 5, 2020

(54) FUEL SENDING UNIT FOR FUEL-TYPE DETECTION

(71) Applicant: Toyota Motor Engineering & Manufacturing North America, Inc., Erlanger, KY (US)

(72) Inventor: Heraldo F. Stefanon, Dexter, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 195 days.

(21) Appl. No.: 15/829,150

(22) Filed: Dec. 1, 2017

(65) Prior Publication Data

US 2019/0170722 A1    Jun. 6, 2019

(51) Int. Cl.
| | |
|---|---|
| G01N 33/22 | (2006.01) |
| G01N 9/36 | (2006.01) |
| G01N 9/16 | (2006.01) |
| G01N 9/12 | (2006.01) |
| G01N 9/10 | (2006.01) |
| G01F 23/00 | (2006.01) |
| G01F 23/30 | (2006.01) |
| F02M 37/00 | (2006.01) |

(52) U.S. Cl.
CPC ......... *G01N 33/22* (2013.01); *F02M 37/0082* (2013.01); *G01F 23/0038* (2013.01); *G01F 23/30* (2013.01); *G01N 9/10* (2013.01); *G01N 9/12* (2013.01); *G01N 9/16* (2013.01); *G01N 9/36* (2013.01)

(58) Field of Classification Search
CPC .. G01N 9/12; G01N 9/16; G01N 9/36; G01N 9/00; G01N 33/22; G01N 9/10; G01F 23/0038; G01F 23/30; G01F 23/64; F02M 37/0082; Y10T 137/3068; Y10T 137/7323
USPC ... 73/444, 448, 451–454, 32 R, 53.01, 61.51
See application file for complete search history.

(56) References Cited

U.S. PATENT DOCUMENTS

| | | | |
|---|---|---|---|
| 2,715,831 A | 8/1955 | Catford et al. | |
| 3,215,185 A | 11/1965 | Black | |
| 5,303,685 A * | 4/1994 | Forgacs | B60K 15/06 123/510 |
| 7,406,871 B2 | 8/2008 | Sugiura | |

(Continued)

OTHER PUBLICATIONS

Mustafa Ertunc Tat et al., "Biodiesel Blend Detection Using a Fuel Composition Sensor," AESA (2001) http://web.cals.uidaho.edu/biodiesel/files/2013/08/ASABE-01-6052.pdf.

(Continued)

*Primary Examiner* — Daniel S Larkin
*Assistant Examiner* — Anthony W Megna Fuentes
(74) *Attorney, Agent, or Firm* — Christopher G. Darrow; Darrow Mustafa PC

(57) ABSTRACT

A method and device are disclosed for fuel-detection by a fuel sending unit by placing a fuel sending unit in a first position from a second position, and releasing the fuel sending unit from the first position such that a buoyancy characteristic of a fuel sending unit float prompts the fuel sending unit to the second position. A rate-of-travel of the fuel sending unit is sensed from the first position to the second position to produce fluid travel data, wherein the rate-of-travel being affected by a fuel density. Fluid-type identification data may be generated based on the fluid travel data.

20 Claims, 4 Drawing Sheets

(56) References Cited

U.S. PATENT DOCUMENTS

| | | | | |
|---|---|---|---|---|
| 2004/0111210 A1* | 6/2004 | Davis | ............. | F02D 19/027 |
| | | | | 701/103 |
| 2004/0182150 A1* | 9/2004 | Okada | ............. | G01F 23/36 |
| | | | | 73/313 |
| 2005/0210963 A1* | 9/2005 | Yekutiely | ............. | G01F 23/40 |
| | | | | 73/53.01 |
| 2006/0137429 A1* | 6/2006 | Henschel | ............. | G01F 23/32 |
| | | | | 73/1.73 |
| 2006/0248952 A1* | 11/2006 | Jarvie | ............. | G01F 23/2963 |
| | | | | 73/444 |
| 2007/0054570 A1* | 3/2007 | Muramatsu | ............. | F02D 9/1065 |
| | | | | 440/87 |
| 2009/0000375 A1* | 1/2009 | Johnson | ............. | G01F 23/363 |
| | | | | 73/317 |
| 2014/0224011 A1* | 8/2014 | Burlage | ............. | G01F 23/0038 |
| | | | | 73/317 |
| 2014/0366843 A1 | 12/2014 | Halleberg | | |
| 2015/0300935 A1* | 10/2015 | Chen | ............. | G01N 9/12 |
| | | | | 73/453 |
| 2016/0238426 A1* | 8/2016 | Tetil | ............. | G01F 23/0038 |

OTHER PUBLICATIONS

Density Sensor for Fuel Quality Monitoring, Integrated Sensing Solutions (webpage, accessed Jul. 17, 2017) (the ISS NPL) http://metersolution.com/using-a-density-sensor-for-fuel-quality-monitoring/.

* cited by examiner vehicle control unit 130

FUEL SENDING UNIT FOR FUEL-TYPE DETECTION

FIELD

The subject matter described herein relates in general to fuel type identification and, more particularly, to detection of a liquid fuel type held in a vehicle fuel tank.

BACKGROUND

Closed loop fuel control systems are generally used in petroleum-powered vehicles to maintain an operating air-fuel (A/F) ratio at stoichiometry. Stoichiometric values, however, can vary with fuel composition. For example, when fuel is added to a vehicle fuel tank, it mixes with fuel already in the tank. For example, ethanol or gasohol in varying mixtures can be added to gasoline already in the tank. If the added fuel has a different composition from that of the fuel already in the tank, the engine of the vehicle may need to operate at a different stoichiometric value after the refueling. Generally, manufactured vehicles may include an emissions sensor that senses the vehicle fuel type and/or composition, and such information to other systems in the vehicle. Because an unknown fuel type and/or composition has entered and been consumed by the vehicle engine, the air-fuel ratio may be adjusted in an after-the-fact manner, which can generate unwanted emission quantities and poor performance until the air-fuel ratio can be optimized for the fuel type.

SUMMARY

A device and method for fuel-type detection are disclosed.

In one implementation, a method for fuel-type detection is disclosed. The method includes placing a fuel sending unit in a first position from a second position, and releasing the fuel sending unit from the first position such that a buoyancy characteristic of a fuel sending unit float prompts the fuel sending unit to the second position. A rate-of-travel of the fuel sending unit is sensed from the first position to the second position to produce fluid travel data, wherein the rate-of-travel being affected by a fuel density. Fluid-type identification data is generated based on the fluid travel data.

In another implementation, a fuel sending unit for fuel-type detection is disclosed. The fuel sending unit includes a fuel sending unit arm, a fuel sending unit float, a servomechanism, and a variable resistor. The fuel sending unit arm being operable to be coupled at a first end to pivot between a first position and a second position. The fuel sending unit float is coupled to a second end of the fuel sending arm for indicating a fuel level, the fuel sending unit float having a buoyancy characteristic to prompt the fuel sending unit arm to the second position. The servomechanism is coupled to the fuel sending unit arm, wherein the servomechanism is operable, in response to a command, to place the fuel sending unit arm in the first position, and to release the fuel sending unit arm from the first position such that the buoyancy characteristic of the fuel sending unit float prompts the fuel sending unit to the second position. The variable resistor is coupled for varying a resistance value relating to a position of the fuel sending unit arm via the fuel sending unit float, wherein the variable resistor is communicatively coupled to a terminal for sensing the resistance value over time to produce rate-of-travel data relating to movement of the fuel sending unit arm from the first position to the second position.

BRIEF DESCRIPTION OF THE DRAWINGS

The description makes reference to the accompanying drawings wherein like reference numerals refer to like parts throughout the several views, and wherein.

DETAILED DESCRIPTION

Fuel-type detection of the contents of a fuel tank is described herein. One example method includes placing a fuel sending unit in a first position from a second position, where the second position may indicate a fuel level. The placement may occur via a servomechanism in response to a command, the servomechanism being coupled about a pivot axis of the fuel sending unit arm to place the fuel sending unit into the first position.

From the first position, the fuel sending unit may be released such that a buoyancy characteristic of a fuel sending unit float prompts the fuel sending unit to the second position. A rate-of-travel of the fuel sending unit from the first position to the second position, where the rate-of-travel is affected by a fuel density of the fuel. That is, the rate-of-travel relates to fuel density, and is affected by the fuel composition of the vehicle fuel tank. In this respect, the fuel type may be detected. Based on the detected fuel-type, base map settings may be selected and provided to a vehicle power train to improve and/or optimize power train performance as relating to the fuel type.

Figure 1:
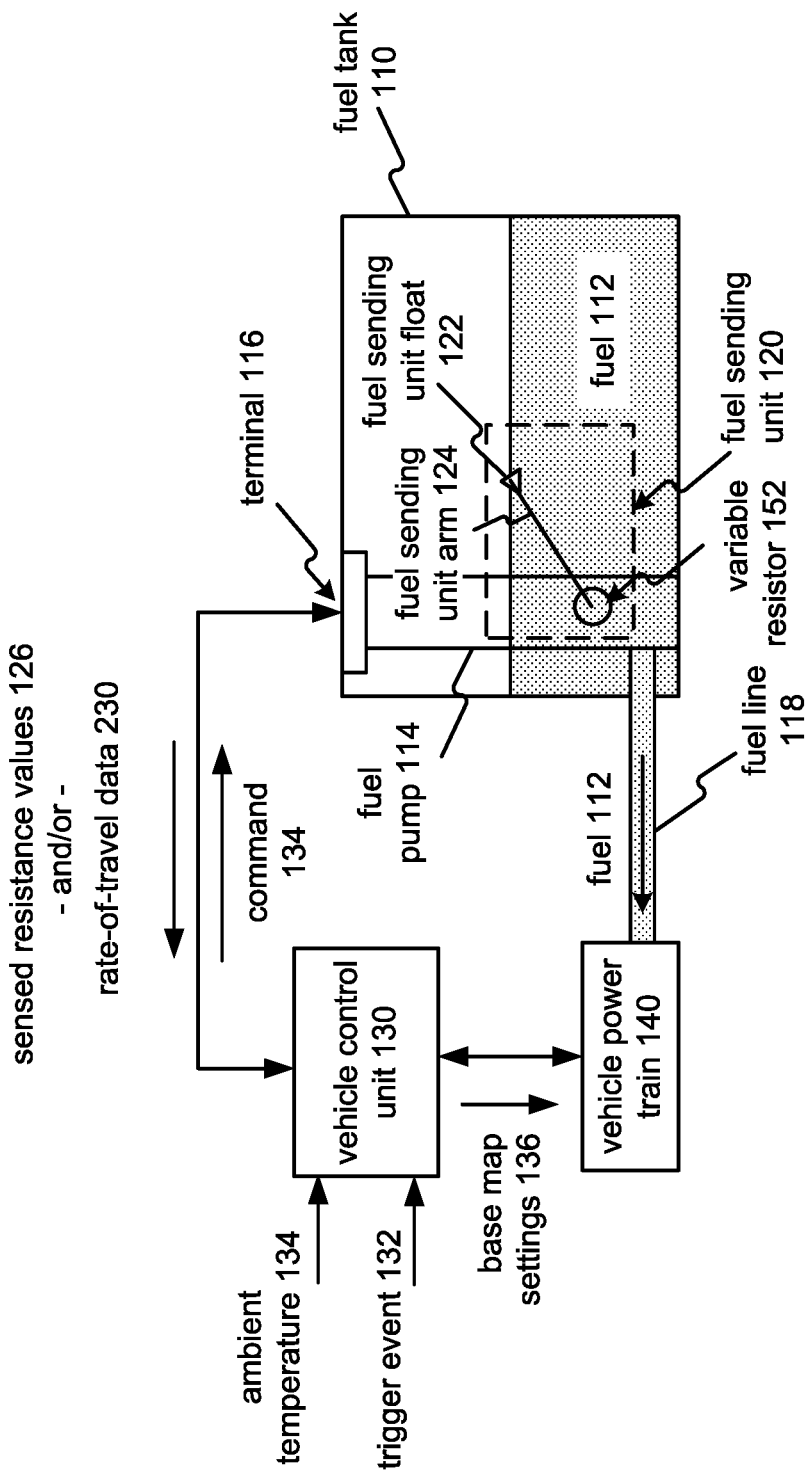
FIG. 1 illustrates a schematic diagram showing a fuel sending unit for fuel-type detection to generate base map settings for a vehicle power train.

FIG. 1 illustrates a schematic diagram showing a fuel sending unit 120 for fuel-type detection to generate base map settings 136 for a vehicle power train 140. The fuel sending unit 120 may accompany a fuel pump 114 received by a fuel tank 110. The fuel tank 110 may be coupled with a vehicle power train 140 via a fuel line 118 to deliver fuel 112. Also, as may be understood, the device and methods of the embodiments herein may be applied to various fuel tank configurations and/or volumes.

The fuel tank 110 may hold any of a plurality of fuels, such as gasoline, light oil, kerosene, vegetable oil, biodiesel, methyl tertiary butyl ether (MTBE), ethanol-blends, and the like.

In operation, the fuel sending unit 120 senses a fuel level, which may be indicated to a vehicle user via a fuel gauge indicator (not shown) on a vehicle dashboard. The fuel sensing unit 120 may include a fuel sensing unit float 122 coupled with a variable resistor 152. Though the fuel sensing unit float 122 may be depicted as having a triangular profile, it may be appreciated that the fuel sensing unit float 122 may include those floats having different profiles, buoyancies, compositions, etc., for use with the embodiments discussed herein.

As may be appreciated, the variable resistor 152 restricts current flow in an electrical circuit without switching off the current. A variable resistor allows more control over current flow by changing the amount of resistance via the fuel sending unit float 122. When resistance increases in a variable resistor, the amount of current that is allowed to flow in a circuit decreases. The variable resistor 152 may include a resistive material or element, and a wiper or brush to set the resistance. Examples of variable resistors can include potentiometers, trimmer, magnetoresistance-based, etc.

As the fuel tank 110 empties, the fuel sending unit float 122 drops and slides a moving contact along the variable resistor 152, which may increase or decrease resistance based upon the desired relation to indicate the fuel level via the fuel gauge. As an example, as the fuel level drops, the resistance of the variable resistor 152 may increase, diminishing the current level.

Respectively, a fuel gauge (not shown) responds to the amount of electric current flowing through the fuel sending unit 120. For example, when the fuel level is high and maximum current is flowing, the fuel gauge may indicate a full tank. When the tank is empty and the least current is flowing, the fuel gauge indicates an empty tank.

The fuel pump 114 may operate to provide the fuel 112, via a fuel line 118, to the vehicle power train 140. The vehicle control unit 130 may operate to detect the fuel-type of the fuel 112 by issuing a command 134 to place the fuel sending unit 120 in a first position, or a position indicating a low fuel condition. In this respect, the fuel sending unit float 122 may be submerged in the fuel 112 by a servomechanism imparting a rotational force to the fuel sending unit arm 124 in response to the command 134, as is discussed in detail with reference to FIGS. 2-4.

The fuel sending unit arm 124 may be released from the first position such that a buoyancy characteristic of the fuel sending unit float 122 prompts the fuel sending unit 120 to the second position, which generally indicates the fuel level of the fuel tank 110. As may be appreciated, a buoyancy characteristic of the fuel sending unit float 122 prompts the fuel sending unit 120 to the second position. In the second position, the fuel sending unit float may experience a null net force. That is, the fuel sending unit float 122 may float on top of the fuel 112, or may be partially-submerged in the fuel 112 in view of the buoyancy characteristic. In an empty tank state, the fuel sending unit float 122 may be retained in place during a fuel fill-up, so that it may be released when a sufficient fuel level exists to determine the fuel-type of the tank contents.

As may be appreciated, the fuel sending unit float 122 may remain submerged upon reaching a travel limit of the fuel sending unit arm 124. For example, the fuel level of the fuel 112 may exceed the travel limit of the fuel sending unit arm 124. The sensed resistance value 126 in turn remains at a low level, indicating a full tank, until the level of the fuel 112 drops below a travel limit of the arm 124.

For example, the vehicle control unit 130 may operate to detect the fuel-type of the fuel 112 based on a trigger event 132, such as a vehicle refueling, a sensed vehicle ignition key, a sensed vehicle door opening, etc. Also, as may be appreciated, to optimize performance of the vehicle power train 140, the trigger event 132 may include a predetermined time period, a random time period, etc.

When released from the first position, a buoyancy characteristic of the fuel sending unit float 122 prompts the fuel sending unit 120 to the second position. In this respect, the vehicle control unit 130 may receive sensed resistance value 126 over time to produce a rate-of-travel of the fuel sending unit 120 from a first position to a second position, which in turn may be used to produce fluid travel data. The fuel density of the fuel 112 affects the rate-of-travel. In this regard, different fuel types may include different fuel densities. Based on the rate-of-travel, which may indicate speed, time, pattern, etc., of the fuel sending unit float 122 movement through the fuel 112), fluid-type data may be generated based on the fluid travel data.

The fluid-type data may be based on the vehicle control unit 130 accessing a look-up table indexed by the fluid travel data. Also, as a density of the fuel 112 may be affected by ambient temperature, the vehicle control unit may sense an ambient temperature 134, to further index the fluid travel data for further accuracy in determining the fluid type to generate base map settings 136 for the operation of the vehicle power train 140 in view of the fuel type of the fuel 112, as is discussed in detail with reference to FIGS. 2-4.

Figure 2:
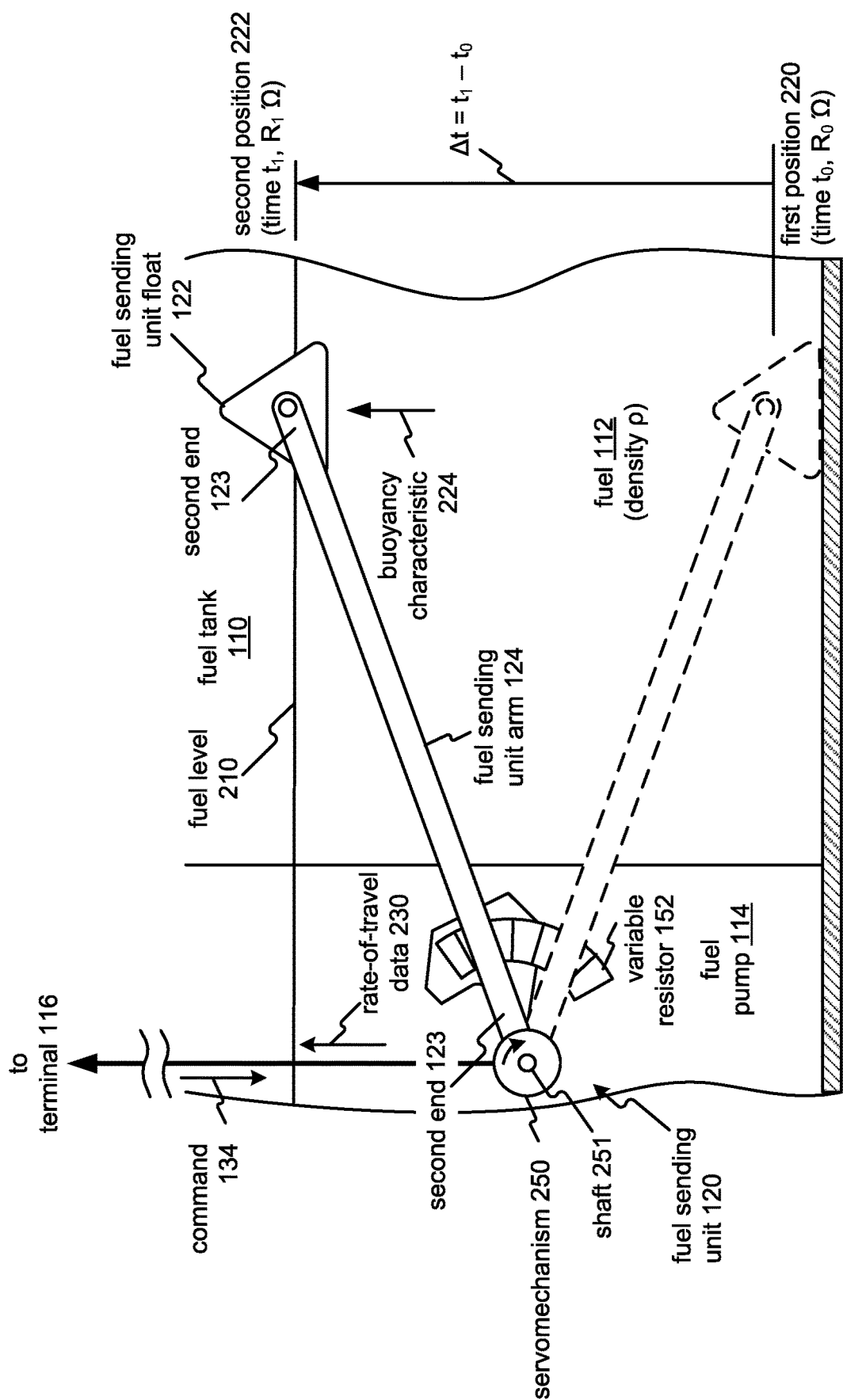
FIG. 2 illustrates a schematic diagram of the fuel sending unit of FIG. 1.

FIG. 2 illustrates a schematic diagram of a fuel sending unit 120. The fuel sending unit 120 may include a fuel sending unit arm 124, a fuel sending unit float 122, a servomechanism 250, and variable resistor 152. For in situ positioning, the fuel sending unit 120 may be co-located with a fuel pump 114 in the fuel tank 110.

The fuel sending unit arm 124 can be operably coupled at a first end 123 to pivot on a shaft 251 between a first position 220 (which may have an associated time to and resistance $R_0$ 'Ω) and a second position 222 (which may have an associated time $t_1$ and resistance $R_1$ 'Ω).

The fuel sending unit float 122 may be coupled to the second end 123 of the fuel sending arm 124 for indicating a fuel level 120. The fuel sending unit float 122 may include a buoyancy characteristic 224 to prompt the fuel sending unit arm 124 to the second position 222 from the first position 220. As may be appreciated, the buoyancy characteristic 224 relates to the behavior of the float 122 when submerged in the fuel 112. When the fuel sending unit float 122 is completely or partially submerged in a the fuel 112, having a density ρ, the float 122 experiences upward force, or buoyancy characteristic 224, that is equal in magnitude to the weight of the fuel displaced by the float 122. The buoyancy characteristic 224 may be considered as being due to the difference between a pressure at the bottom of the float 122, and pressure at the top pushing down.

At the fuel level 210, the fuel sending unit float 122 may float on top of the fuel 112, or may be partially-submerged in the fuel 112 in view of the buoyancy characteristic 224. That is, the fuel sending unit float 122 may experience a null net force.

As may be appreciated, the fuel sending unit float 122 may also remain submerged upon reaching a travel limit of the fuel sending unit arm 124. For example, the fuel level of the fuel 112 may exceed the travel limit of the fuel sending unit arm 124. The sensed resistance value 126 in turn remains at a low level, indicating a full tank, until the level of the fuel 112 drops below a travel limit of the arm 124.

The servomechanism 250 may be coupled at a second end 123 of the fuel sending unit arm 124, and to a shaft 251. The servomechanism may place the shaft 251, and the fuel sending unit arm 124, which is in a fixed relation with the shaft 251, to specific angular position of the first position 220 via the command 134. While the command 134 is present, the servomechanism may maintain the first position 220.

When the command 134 is released, the angular position may be no longer maintained to release the fuel sending unit arm 124 from the first position 220 such that the buoyancy characteristic 224 of the fuel sending unit float 122 prompts the fuel sending unit 120 to the second position 222.

The rate-of-travel 230, as sensed by the vehicle control unit 130 via terminal 116 may be based on a rate of change in resistance (such as from resistance $R_0$ 'Ω to resistance $R_1$ 'Ω) over time (such a time $t_0$ to time $t_1$, or $\Delta t$) from the first position 220 to the second position 222. The rate-of-travel 230 may also be based on a rate of change in electric current as the resistance changes (such as from resistance $R_0$ 'Ω to resistance $R_1$ 'Ω) over time (such a time $t_0$ to time $t_1$, or $\Delta t$) from the first position 220 to the second position 222.

The variable resistor 152 may be coupled for varying a resistance value relating to a position of the fuel sending unit arm 124 via the fuel sending unit float 122. The variable resistor 152 is communicatively coupled to a terminal 116, which may be monitored to sense the resistance value or to sense the electric current value (such as from resistance $R_0$ 'Ω to resistance $R_1$ 'Ω) over time (such a time $t_0$ to time $t_1$, or $\Delta t$) to produce rate-of-travel data 230 relating to movement of the fuel sending unit arm 124 from the first position 220 to the second position 222.

The rate-of-travel data 230 operates to identify a fuel type of the fuel 112 in relation to the density ρ. That is, the higher the density, the larger the value of $\Delta t$. The lower the density, the smaller the value of $\Delta t$. Fuels such as ethanol, biodiesel, butanol and Fischer-Tropsch fuels, etc., have varying densities, calling for appropriate engine base map settings in view of the fuel characteristics identified via the fuel sending unit 120.

As an example, gasoline may have a density range of 0.725 to 0.775 gm/cc, E85 may have a density range of 0.775 to 0.782 gm/cc, ethanol a density of 0.7856 gm/cc, Fisher Topsch Diesel may have a density range of 0.784 to 0.801 gm/cc, diesel may have a density range of 0.822 to 0.860 gm/cc, biodiesel may have a density range of 0.860 to 0.900 gm/cc, etc. Rate-of-travel data 230 differs for the plurality of fuels that may provide fuel 112 of the fuel tank 110. In this respect, a vehicle power train may be powered by several types of fuel.

Such vehicles may also be referred to flexible-fuel vehicle (FFV) or dual-fuel vehicle, which is an alternative fuel vehicle with an internal combustion engine that may be powered by more than one fuel type, such as gasoline blended with either ethanol or methanol fuel, and both fuels may be stored in the fuel tank 110. Also, as engine combustion technologies advance (such as gasoline and/or diesel fuels being available for a combustible fuel), other seemingly incompatible fuel types may be used to power vehicle power train. Flex-fuel power trains are capable of burning any proportion of the resulting blend in the combustion chamber as fuel injection and spark timing are adjusted via base map settings 136 (FIG. 1) based on to the fuel-type (or blend) detected by the fuel sending unit 120 as set out herein. The fuel type may be further refined in view of the ambient temperature data that may also affect density of the various fuel types.

Figure 3:
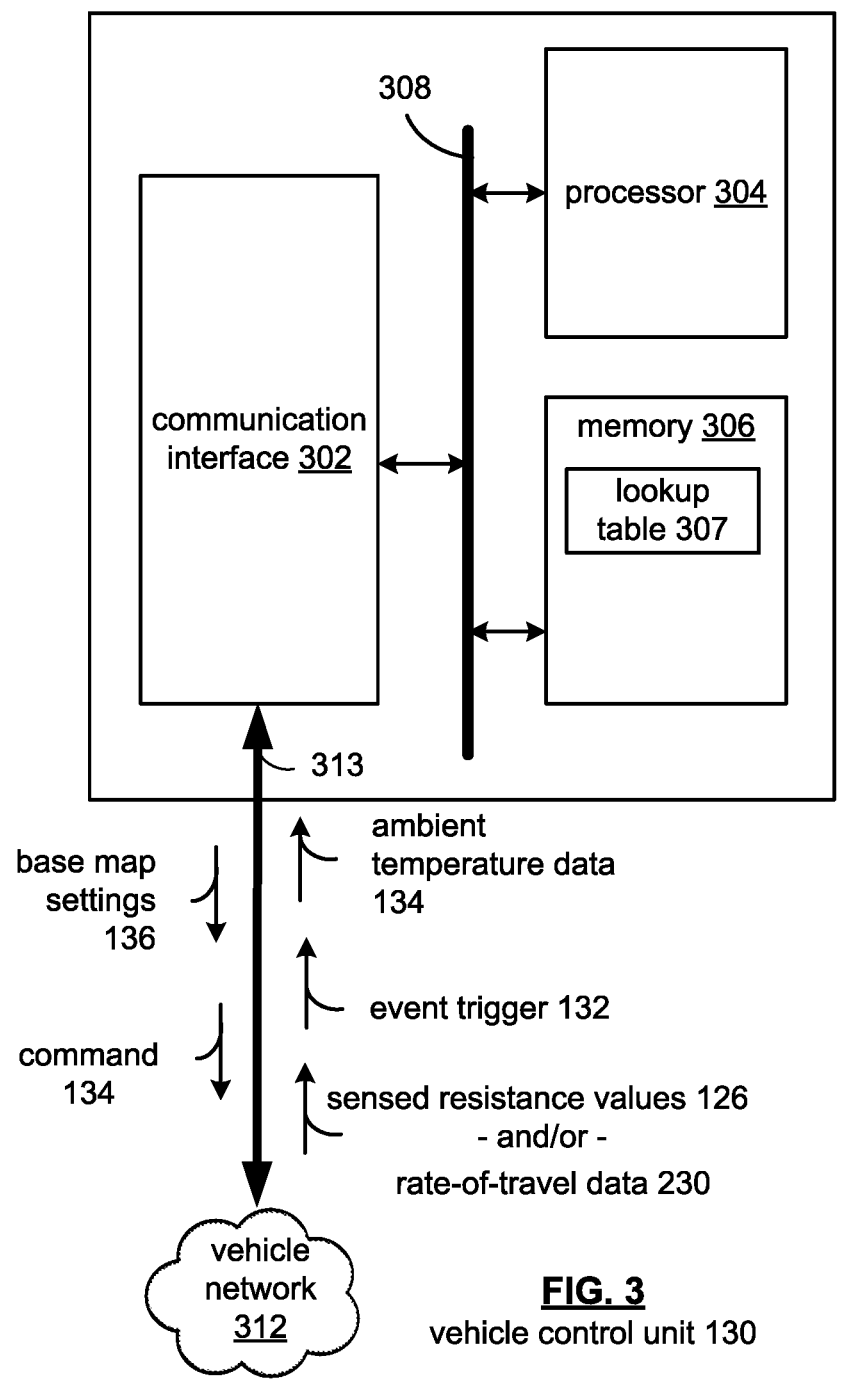
FIG. 3 illustrates a block diagram of the vehicle control unit of FIG. 1.

FIG. 3 illustrates a block diagram of the vehicle control unit 130, which includes a communication interface 302, a processor 304, and memory 306, that are communicatively coupled via a bus 308.

The processor 304 in the vehicle control unit 130 can be a conventional central processing unit or any other type of device, or multiple devices, capable of manipulating or processing information. As may be appreciated, processor 304 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions.

The memory and/or memory element 306 may be a single memory device, a plurality of memory devices, and/or embedded circuitry of the processor 304. Such a memory device may be a read-only memory, random access memory, volatile memory, non-volatile memory, static memory, dynamic memory, flash memory, cache memory, and/or any device that stores digital information. The memory 306 is capable of storing machine readable instructions such that the machine readable instructions can be accessed by the processor 304.

The machine readable instructions can comprise logic or algorithm(s) written in programming languages, and generations thereof, (e.g., 1GL, 2GL, 3GL, 4GL, or 5GL) such as, for example, machine language that may be directly executed by the processor 204, or assembly language, object-oriented programming (OOP), scripting languages, microcode, etc., that may be compiled or assembled into machine readable instructions and stored on the memory 306. Model-Based Design (MBD) may also used with respect to generating machine readable instructions that may be stored on the memory 306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods and devices described herein may be implemented in any conventional computer programming language, as pre-programmed hardware elements, or as a combination of hardware and software components.

Memory 306 may also store lookup table 307, which may be accessed based on rate-of-travel data 230 to identify a fuel type of the fuel 112 (FIG. 2) in relation to the density ρ. Fuels such as ethanol, biodiesel, butanol and Fischer-Tropsch fuels, etc., have varying densities, calling for appropriate engine base map settings in view of the fuel characteristics identified via the fuel sending unit 120.

As an example, gasoline may have a density range of 0.725 to 0.775 gm/cc, E85 may have a density range of 0.775 to 0.782 gm/cc, ethanol a density of 0.7856 gm/cc, Fisher Topsch Diesel may have a density range of 0.784 to 0.801 gm/cc, diesel may have a density range of 0.822 to 0.860 gm/cc, biodiesel may have a density range of 0.860 to 0.900 gm/cc, etc. Rate-of-travel data 230 differs for the plurality of fuels that may provide fuel 112 of the fuel tank 110. In this respect, a vehicle power train may be powered by several types of fuel.

Such vehicles may also be referred to flexible-fuel vehicle (FFV) or dual-fuel vehicle, which is an alternative fuel vehicle with an internal combustion engine that may be powered by more than one fuel type, such as gasoline blended with either ethanol or methanol fuel, and both fuels may be stored in the fuel tank 110. Flex-fuel power trains are capable of burning any proportion of the resulting blend in the combustion chamber as fuel injection and spark timing are adjusted via base map settings 136 (FIG. 1) based on to the fuel-type (or blend) detected by the fuel sending unit 120 as set out herein. The fuel type may be further refined in view of the ambient temperature data 134 that may also affect density of the various fuel types.

In this respect, the look-up table 307 may be used to determine a fuel-type in view of the rate-of-travel data 230, and further in view of the ambient temperature data 134.

Note that when the processor 304 includes more than one processing device, the processing devices may be centrally located (e.g., directly coupled together via a wired and/or wireless bus structure) or may be distributed located (e.g., cloud computing via indirect coupling via a local area network and/or a wide area network). Further note that when the processor 304 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element stores, and the processor 304 executes, hard coded and/or operational instructions corresponding to at least some of the steps and/or functions illustrated in FIGS. 1-4 to perform fuel-type detection features and methods described herein.

The communication interface 302 generally governs and manages the input data via the vehicle network 312 over the communication path 313. The communication interface 302 also manages controller unit output data such as command 134 to detect a fuel-type of a fuel, and the base map settings 136 for a vehicle power train based on the detected fuel-type. The communication interface 302 also manages input data, such as trigger event 132, ambient temperature 134, sensed resistance values 126 and/or rate-of-travel data 230.

There is no restriction on the present disclosure operating on any particular hardware arrangement and therefore the basic features herein may be substituted, removed, added to, or otherwise modified for improved hardware and/or firmware arrangements as they may develop.

The vehicle control unit 130 may operate to generate base map settings 136 based on command 134. The command 134 may be generated based on a trigger event 132, such as a vehicle refueling, a sensed vehicle ignition key, a sensed vehicle door opening, etc. Also, as may be appreciated, to optimize performance of the vehicle power train 140, the trigger event 132 may include a predetermined time period, a random time period, etc.

The vehicle control unit 130 functions to receive sensed resistance values 126 and/or rate-of-travel data 230 for optimizing performance of a vehicle power train 140 (FIG. 1) in view of the methods and devices for fuel-type detection provided herein.

Figure 4:
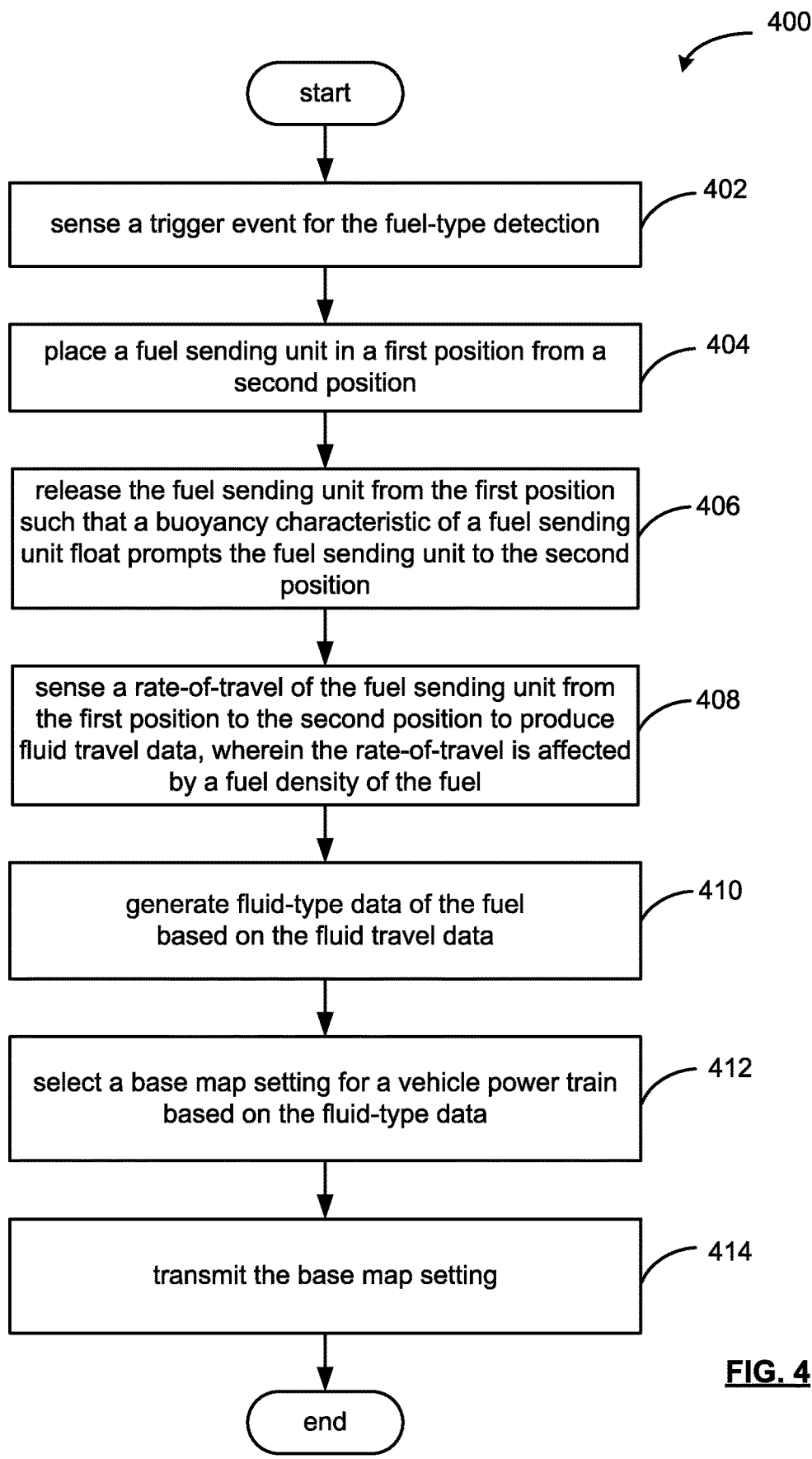
FIG. 4 shows an example process for fuel-type detection via a fuel sending unit.

FIG. 4 shows an example process 400 for fuel-type detection via a fuel sending unit. At operation 402 a trigger event for fuel-type detection is sensed. A trigger event may include a vehicle refueling, a sensed vehicle ignition key, a sensed vehicle door opening, etc. Also, as may be appreciated, the trigger event may include a predetermined time period, a random time period, etc.

At operation 404, responsive to the trigger event, a fuel sending unit is placed in a first position from a second position, where the second position may indicate a fuel level of a fuel of a plurality of fuels to be detected and/or determined. Placement of the fuel sending unit may be provided via a servomechanism coupled to a fuel sending unit arm, and to a shaft. For example, servomechanism may place the shaft, and the fuel sending unit arm, which is in a fixed relation with the shaft, to a specific angular position relating to the first position.

At operation 406, the fuel sending unit may be released from the first position such that a buoyancy characteristic of a fuel sending unit float prompts the fuel sending unit to the second position. Such a release may result from releasing the servomechanism to allow the buoyancy characteristic 224 of the fuel sending unit float travel to the second position.

A rate-of-travel of the fuel sending unit from the first position to the second position is sensed to produce fluid travel data at operation 408, wherein the rate-of-travel is affected by a fuel density of the fuel.

At operation 410, fluid-type data of the fuel is based on the fluid travel data, in which the fuel-type is detected, which may be provided by accessing a look-up table. Fuels such as ethanol, biodiesel, butanol and Fischer-Tropsch fuels, etc., have varying densities, calling for appropriate engine base map settings in view of the fuel characteristics identified via the fuel sending unit.

As an example, gasoline may have a density range of 0.725 to 0.775 gm/cc, E85 may have a density range of 0.775 to 0.782 gm/cc, ethanol a density of 0.7856 gm/cc, Fisher Topsch Diesel may have a density range of 0.784 to 0.801 gm/cc, diesel may have a density range of 0.822 to 0.860 gm/cc, biodiesel may have a density range of 0.860 to 0.900 gm/cc, etc. Rate-of-travel data 230 differs for the plurality of fuels that may provide fuel 112 of the fuel tank 110. In this respect, a vehicle power train may be powered by several types of fuel.

Such vehicles may also be referred to flexible-fuel vehicle (FFV) or dual-fuel vehicle, which is an alternative fuel vehicle with an internal combustion engine that may be powered by more than one fuel type, such as gasoline blended with either ethanol or methanol fuel, and both fuels may be stored in a fuel tank. Flex-fuel power trains are capable of burning any proportion of the resulting blend in the combustion chamber as fuel injection and spark timing are adjusted via base map settings of operation 412, based on to the fuel-type (or blend) detected via the fuel sending unit as set out herein.

The fuel type may be further refined in view of the ambient temperature data that may also affect a density of the various fuel types.

In this respect, the look-up table may be used to determine a fuel-type in view of the rate-of-travel data, and further in view of the ambient temperature data.

At operation 412, a base map setting may be selected for a vehicle power train based on the fluid-type data, and transmitted at operation 414 to effect the selected base map setting.

While particular combinations of various functions and features of the present invention have been expressly described herein, other combinations of these features and functions are possible that are not limited by the particular examples disclosed herein are expressly incorporated within the scope of the present invention.

As one of ordinary skill in the art may further appreciate, the term "coupled," as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of ordinary skill in the art will also appreciate, inferred coupling (that is, where one element is coupled to another element by inference) includes direct and indirect coupling between two elements in the same manner as "coupled."

The foregoing description relates to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretations so as to encompass all such modifications and equivalent structures as is permitted under the law.

What is claimed is:

1. A method for fuel-type detection comprising:
 placing a fuel sending unit in a first position from a second position, the second position indicating a fuel level;

releasing the fuel sending unit from the first position such that a buoyancy characteristic of a fuel sending unit float prompts the fuel sending unit to the second position;

sensing a rate-of-travel of the fuel sending unit from the first position to the second position to produce fluid travel data, the rate-of-travel being affected by a fuel density; and generating fuel-type identification data based on the fluid travel data.

2. The method of claim 1, wherein the placing a fuel sending unit in the first position from the second position comprises actuating a servo operably coupled to an arm of the fuel sending unit.

3. The method of claim 1, wherein the generating the fuel-type-data from the fluid travel data further comprises:
accessing a look-up table indexed by the fluid travel data.

4. The method of claim 3, wherein the accessing the look-up table further comprises:
sensing an ambient temperature to produce ambient temperature data; and
accessing the look-up table being further indexed by the ambient temperature data.

5. The method of claim 1, wherein the sensing the rate-of-travel of the fuel sending unit from the first position to the second position to produce fluid travel data comprises at least one of:
sensing a variation in resistance, via a variable resistor of the fuel sending unit, over time; and
sensing a change in current, via the variable resistor of the fuel sending unit, over time.

6. The method of claim 1, wherein at the second position the fuel sending unit float experiences a null net force.

7. A method for fuel-type detection for a vehicle engine comprising:
sensing a trigger event for the fuel-type detection;
placing, in response to the trigger event, a fuel sending unit in a first position from a second position, the second position indicating a fuel level of a fuel of a plurality of fuels;
releasing the fuel sending unit from the first position such that a buoyancy characteristic of a fuel sending unit float prompts the fuel sending unit to the second position;
sensing a rate-of-travel of the fuel sending unit from the first position to the second position to produce fluid travel data, wherein the rate-of-travel is affected by a fuel density of the fuel;
generating fuel-type data of the fuel based on the fluid travel data; and
selecting a base map setting for a vehicle power train based on the fuel-type data.

8. The method of claim 7, wherein the trigger event comprises at least one of:
a vehicle refueling;
a sensed vehicle ignition key;
a sensed vehicle door opening;
a predetermined time period; and
a random time period.

9. The method of claim 7, wherein the placing the fuel sensing unit in the first position from the second position comprises actuating a servomechanism operably coupled to a fuel sending unit arm.

10. The method of claim 7, wherein the generating the fuel-type data from the fluid travel data further comprises:
accessing a look-up table based on the fluid travel data.

11. The method of claim 10, wherein the accessing the look-up table further comprises:
sensing an ambient temperature to produce ambient temperature data; and
accessing the look-up table being further based on the ambient temperature data.

12. The method of claim 7, wherein the sensing the rate-of-travel of the fuel sending unit from the first position to the second position to produce the fluid travel data comprises at least one of:
sensing a variation in resistance, via a variable resistor of the fuel sending unit, that corresponds with a movement of the fuel sending unit float from the first position to the second position; and
sensing a change in current, via the variable resistor of the fuel sending unit, that corresponds with a movement of the fuel sending unit float from the first position to the second position.

13. The method of claim 7, wherein at the second position the fuel sending unit float experiences a null net force.

14. A fuel sending unit for fuel-type detection comprising:
a fuel sending unit arm operable to be coupled at a first end to pivot between a first position and a second position;
a fuel sending unit float coupled to a second end of the fuel sending arm for indicating a fuel level, the fuel sending unit float having a buoyancy characteristic to prompt the fuel sending unit arm to the second position;
a servomechanism coupled to the fuel sending unit arm, wherein the servomechanism is operable, in response to a command, to:
place the fuel sending unit arm in the first position; and
release the fuel sending unit arm from the first position such that the buoyancy characteristic of the fuel sending unit float prompts the fuel sending unit to the second position; and
a variable resistor coupled for varying a resistance value relating to a position of the fuel sending unit arm via the fuel sending unit float, wherein the variable resistor is communicatively coupled to a terminal, the terminal for sensing the resistance value over time to produce rate-of-travel data relating to movement of the fuel sending unit arm from the first position to the second position.

15. The fuel sending unit of claim 14, wherein the rate-of-travel data operates to identify a fuel type.

16. The fuel sending unit of claim 14, wherein the rate-of-travel data and ambient temperature data operate to identify a fuel type.

17. The fuel sending unit of claim 14, wherein the variable resistor is coupled to the first end of the fuel sending unit arm.

18. The fuel sending unit of claim 14, wherein the servomechanism further comprises:
an output shaft coupled to the first end of the fuel sending unit arm, wherein in response to the command, the output shaft is positionable at the first position.

19. The fuel sending unit of claim 14, wherein the rate-of-travel data is based on at least one of:
a rate of change in resistance over time from the first position to the second position; and
a rate of change in current over time from the first position to the second position.

20. The fuel sending unit of claim 14, wherein at the second position the fuel sending unit float experiences a null net force.

* * * * *